US011382558B2

(12) United States Patent
Baker et al.

(10) Patent No.: US 11,382,558 B2
(45) Date of Patent: Jul. 12, 2022

(54) SKIN FEATURE IMAGING SYSTEM

(71) Applicant: Welch Allyn, Inc., Skaneateles Falls, NY (US)

(72) Inventors: Steven D. Baker, Beaverton, OR (US); Robert James Kahlke, Milwaukie, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 70 days.

(21) Appl. No.: 16/857,486

(22) Filed: Apr. 24, 2020

(65) Prior Publication Data
US 2020/0261016 A1 Aug. 20, 2020

Related U.S. Application Data

(62) Division of application No. 15/479,904, filed on Apr. 5, 2017, now Pat. No. 10,674,953.

(Continued)

(51) Int. Cl.
*A61B 5/00* (2006.01)
*A61B 5/103* (2006.01)
*A61B 5/107* (2006.01)

(52) U.S. Cl.
CPC ............ *A61B 5/444* (2013.01); *A61B 5/0077* (2013.01); *A61B 5/1032* (2013.01);
(Continued)

(58) Field of Classification Search
CPC ..... A61B 5/444; A61B 5/0077; A61B 5/1032; A61B 5/7221; A61B 5/742; A61B 5/0062; A61B 5/1079
See application file for complete search history.

(56) References Cited

U.S. PATENT DOCUMENTS 7,725,151 B2 * 5/2010 van der Weide .... A61B 5/0062
600/407
8,543,519 B2 * 9/2013 Guyon ................... G16H 50/20
706/12

(Continued)

FOREIGN PATENT DOCUMENTS

| WO | 2009142758 A1 | 11/2009 |
| WO | 2013144184 A2 | 10/2013 |
| WO | 2014108896 A1 | 7/2014 |

OTHER PUBLICATIONS

Kassianos et al., 2015, "Smartphone application for melanoma detection by community, patient and generalist clinician user: a review" (pp. 1507-1518). (Year: 2015).*

(Continued)

*Primary Examiner* — Manav Seth
(74) *Attorney, Agent, or Firm* — Merchant & Gould P.C.

(57) ABSTRACT

An imaging device for monitoring a skin feature includes a camera, at least one processor and memory. The imaging device displays a body area guide, receives a selection of a body area, initiates an image sequence of the body area, the image sequence including capturing, using the camera, a plurality of images, determines whether all body areas have been imaged, analyzes the images, and provides the analyzed images to a clinician. The imaging device can be part of a system including a server in communication with a monitor, where the clinician views the images on the monitor. Additionally, each skin feature can be ranked in order of risk and presented to the clinician in that order.

12 Claims, 9 Drawing Sheets

Related U.S. Application Data

(60) Provisional application No. 62/325,229, filed on Apr. 20, 2016.

(52) U.S. Cl.
CPC .......... *A61B 5/7221* (2013.01); *A61B 5/742* (2013.01); *A61B 5/0062* (2013.01); *A61B 5/1079* (2013.01)

(56) References Cited

U.S. PATENT DOCUMENTS

| | | | |
|---|---|---|---|
| 8,675,920 B2* | 3/2014 | Hanson | A61B 5/0022 382/103 |
| 8,837,832 B2* | 9/2014 | Kislal | G06K 9/00362 382/182 |
| 9,064,304 B2* | 6/2015 | Kenny | G06K 9/00134 |
| 10,674,953 B2* | 6/2020 | Baker | A61B 5/742 |
| 2011/0015494 A1 | 1/2011 | Spaulding | |
| 2011/0040192 A1* | 2/2011 | Brenner | G06T 7/0016 600/476 |
| 2013/0096392 A1 | 4/2013 | Adams | |
| 2013/0225969 A1 | 8/2013 | Bao et al. | |
| 2014/0313303 A1 | 10/2014 | Davis et al. | |
| 2014/0316235 A1 | 10/2014 | Davis et al. | |
| 2014/0350379 A1 | 11/2014 | Verdooner | |
| 2014/0378810 A1 | 12/2014 | Davis et al. | |
| 2015/0005032 A1 | 1/2015 | Fletcher et al. | |
| 2015/0025343 A1 | 1/2015 | Gareau et al. | |
| 2015/0065803 A1 | 3/2015 | Douglas et al. | |
| 2015/0077430 A1 | 3/2015 | Conroy | |
| 2017/0124709 A1* | 5/2017 | Rithe | G06K 9/2036 |

OTHER PUBLICATIONS

Herzer et al., "Semi-Automated Diagnosis of Melanoma Through the Analysis of Dermatological Images" (pp. 71-78). (Year: 2010).*
Okuboyejo et al., "Automating Skin Disease Diagnosis Using Image Classification" (pp. 1-5) (Year: 2013).*
Das et al., "An SVM based skin disease identification using Local Binary Patterns" (pp. 208-211) (Year: 2013).*
Abuzaghleh et al., SKINcure: An Innovative Smart Phone-Based Application to Assist in Melanoma Early Detection and Prevention, University of Bridgeport, Jan. 6, 2015, 15pgs.
Boxall, Use Your Smartphone to Detect Skin Cancer: Help Catch Skin Cancer Early With This Potentially Life-Saving, $100 Smartphone Accessory, Digital Trends, Jun. 10, 2015, 12pgs.
Canfield, Automatic Image Stitching for Vectra H1, Spring 2014 Issue, 3pgs.
Rankov et al., An Algorithm for Image Stitching and Blending, Three-Dimensional and Multidimensional Microscopy Image Acquisition and Processing XII, Proceedings of SPIE—vol. 5701, Mar. 2005, 11 pgs.
Skinvision, Melanoma Skin Cancer Detection App, Jul. 28, 2015, 9pgs.
Reich, The 'Mole Mapper' iPhone App Helps Detect Skin Cancer, Tech Times, Oct. 20, 2015, 3pgs.
Ohsu, Mole Mapper, Oct. 2015, 3pgs.

* cited by examiner

US 11,382,558 B2

SKIN FEATURE IMAGING SYSTEM

CROSS-REFERENCE TO RELATED APPLICATIONS

The present application claims priority to U.S. Provisional Patent Application No. 62/325,229, filed on Apr. 20, 2016, the disclosure of which is hereby incorporated by reference in its entirety.

BACKGROUND

Skin features, such as a nevus (a mole), can change size, shape and color over time. Some skin features can become cancerous or can be indicative of cancer. People can have multiple different skin features on different parts of their bodies. Thus, monitoring skin features can be part of a regimen for people with the skin features.

SUMMARY

Embodiments of the present disclosure are directed to a skin feature imaging system. In one aspect, an imaging device for monitoring a skin feature includes a camera, at least one processor, and memory encoding computer-executable instructions. The computer-executable instructions, when executed by the at least one processor, cause the at least one processor to: display a body area guide, receive a selection of a body area, initiate an image sequence of the body area, where the image sequence includes capturing a plurality of images using the camera. Additionally, the computer-executable instructions, when executed by the at least one processor, cause the at least one processor to determine whether all body areas have been imaged, analyze the plurality of images, and provide the plurality of images to a clinician.

The details of one or more embodiments are set forth in the accompanying drawings and the description below. Other features, objects, and advantages of these embodiments will be apparent from the description, drawings, and claims.

DESCRIPTION OF THE DRAWINGS

The following drawing figures, which form a part of this application, are illustrative of described technology and are not meant to limit the scope of the disclosure as claimed in any manner, which scope shall be based on the claims appended hereto.

DETAILED DESCRIPTION

The present disclosure is directed to imaging and tracking one or more skin features. An example skin feature is a mole (medically, a mole is a nevus, plural nevi; for readability, this disclosure will use "mole" in place of "nevus"). Some people have many moles that require monitoring over time. The moles are monitored for changes which could indicate the moles are becoming tumors or cancerous. An example of relevant mole characteristics is the "ABCDE" analysis of moles: Asymmetry, Border, Color, Diameter, Evolving. That is, if a mole is asymmetrical, has an irregular border, has varied colors, is larger than about 6 mm, or size, shape or color has continued to change, then the mole should be examined by a medical professional such as a dermatologist.

There are other mole characteristics that may be used with the present disclosure. For example, the Blue-Black rule that calls attention to any lesion containing some dark blue and black color that does not resemble the surrounding lesions. Another example is the CUBED guide to early warning signs of nail melanomas, which is different from the ABCDE evaluation. CUBED is an acronym for C=Colored lesions, U=Uncertain diagnosis, B=Bleeding under the nail and the appearance of beefy red tissue, E=Enlargement or deterioration of the lesion or the wound area despite treatment, and D=Delay in healing beyond two months. Another example is the "ugly duckling sign," a method of visual detection based on the concept that melanomas look, feel, or evolve differently than surrounding moles. Yet another example is the EFG evaluation for Nodular Melanomas. The EFG rule is an alternative to the ABCDE evaluation, since nodular melanomas may not be recognizable using the ABCDEs. EFG stands for Elevated, Firm on palpation, and Growing progressively for over a month.

Other characterization methods may be used, including the use of multi-spectral imaging to detect the depth of melanoma penetration. Using longer wavelengths to interrogate the lesion allows detection at deeper levels. A multispectral system may use multiple discrete sources, each of which illuminates the skin at a different wavelength, for example, 470 nm, 591 nm, 631 nm, and 850 nm for blue, yellow, red, and infrared, respectively. A broadband source may be used with filters that allow only the wavelength(s) of interest. The filter may be manually or automatically selected for each wavelength band of interest. A cooled detector allows the system to expand to mid- and far-infrared wavelengths. A system may also use a laser, such as a VCSEL-ULM850-A4 manufactured by Philips Photonics. Lasers provide monochromatic illumination. A system may use an integrated multi-wavelength source such the SFH7050 from Osram Opto Semiconductors. The system may consider the images separately or combine images, for example, to obtain the best contrast of a particular feature. Non-optical frequencies may also be used, for example, RF including ultrawide band and ultrasonic.

Figure 1:
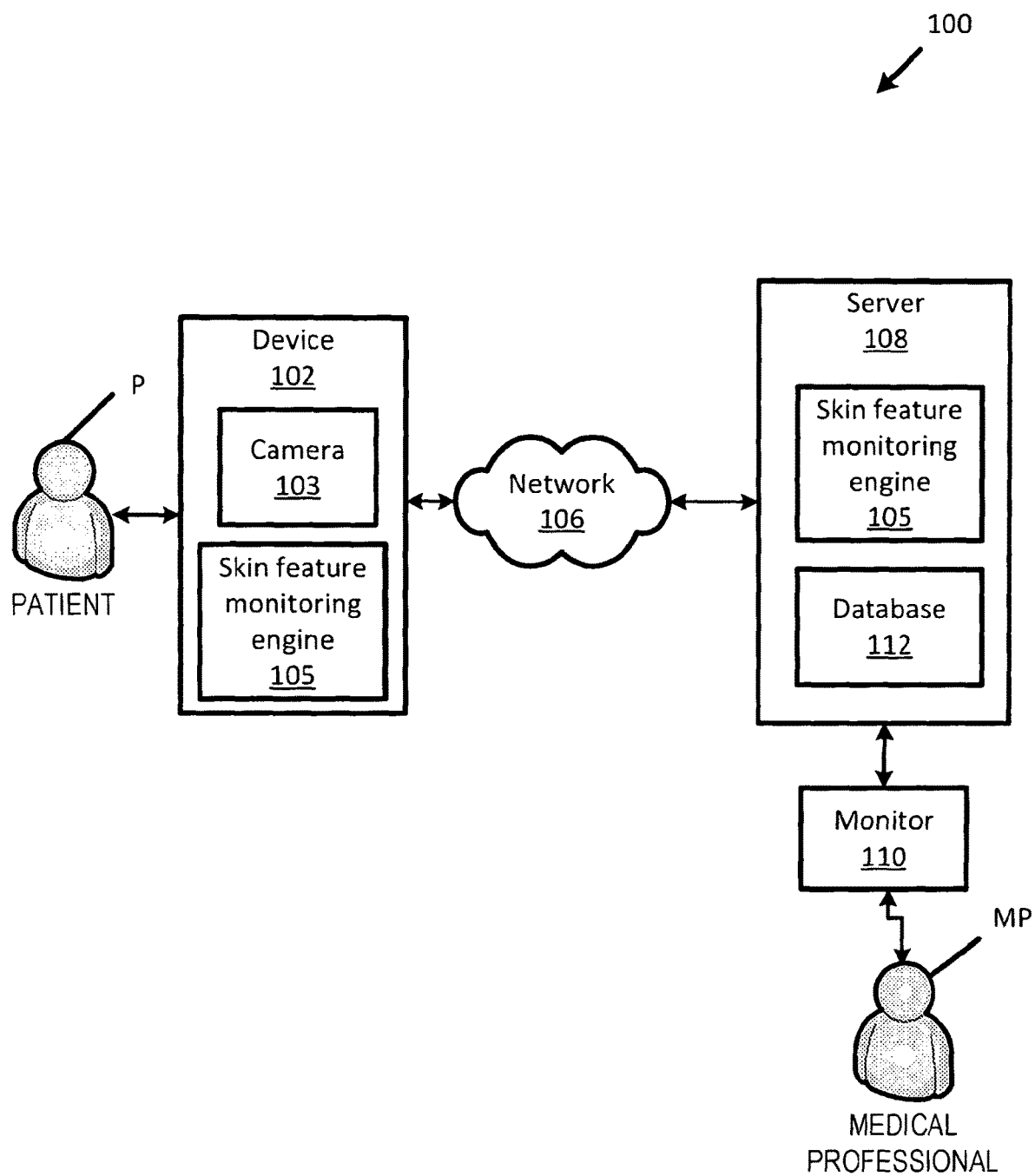
FIG. 1 illustrates an example block diagram of a skin feature imaging system.

FIG. 1 illustrates an example embodiment of a skin feature imaging system 100. The example skin feature imaging system 100 includes a patient P, a medical professional MP, and a device 102 in communication with a server 108 via a network 106. The device 102 includes a camera 103 and a skin feature monitoring engine 105. The server 108 includes the skin feature monitoring engine 105, database 112, and is in communication with a monitor 110. The skin feature imaging system 100 produces and analyzes images of the patient's P skin features, such as moles. The patient P and medical professional MP can be in the same location, such as a clinic exam room, or in remote locations, such as the patient P being located at the patient's P home and the medical professional MP being located at a medical clinic. Other embodiments can include more or fewer people and components.

The medical professional MP uses the skin feature imaging system 100 to screen for, diagnose, or monitor the patient P's moles. In other embodiments, the skin feature imaging system 100 is used to screen for, monitor, or diagnose various other skin conditions and/or diseases, including, but not limited to: the healing of a wound, rashes, dermatofibromas, dermoid cysts, keloids, keratoacanthomas, lipomas, basal cell carcinoma, squamous cell carcinoma, actinic keratosis, ichthyosis, longitudinal melanonychia, subungual melanoma, superficial spreading melanoma and the like. The medical professional MP is a trained and/or certified health professional, such as, for example, a nurse, a nurse practitioner, a physician assistant, a physician, including a dermatologist or an oncologist. Clinician and medical professional are used interchangeably in this disclosure. Example methods of using the skin feature imaging system 100 are shown and described in more detail below with reference to FIGS. 2-8.

The device 102 is used to capture images of the patient's P skin. In embodiments, the patient P operates the device 102. In other embodiments, a friend, family member, medical professional, robot or computer operates the device 102.

Figure 6:
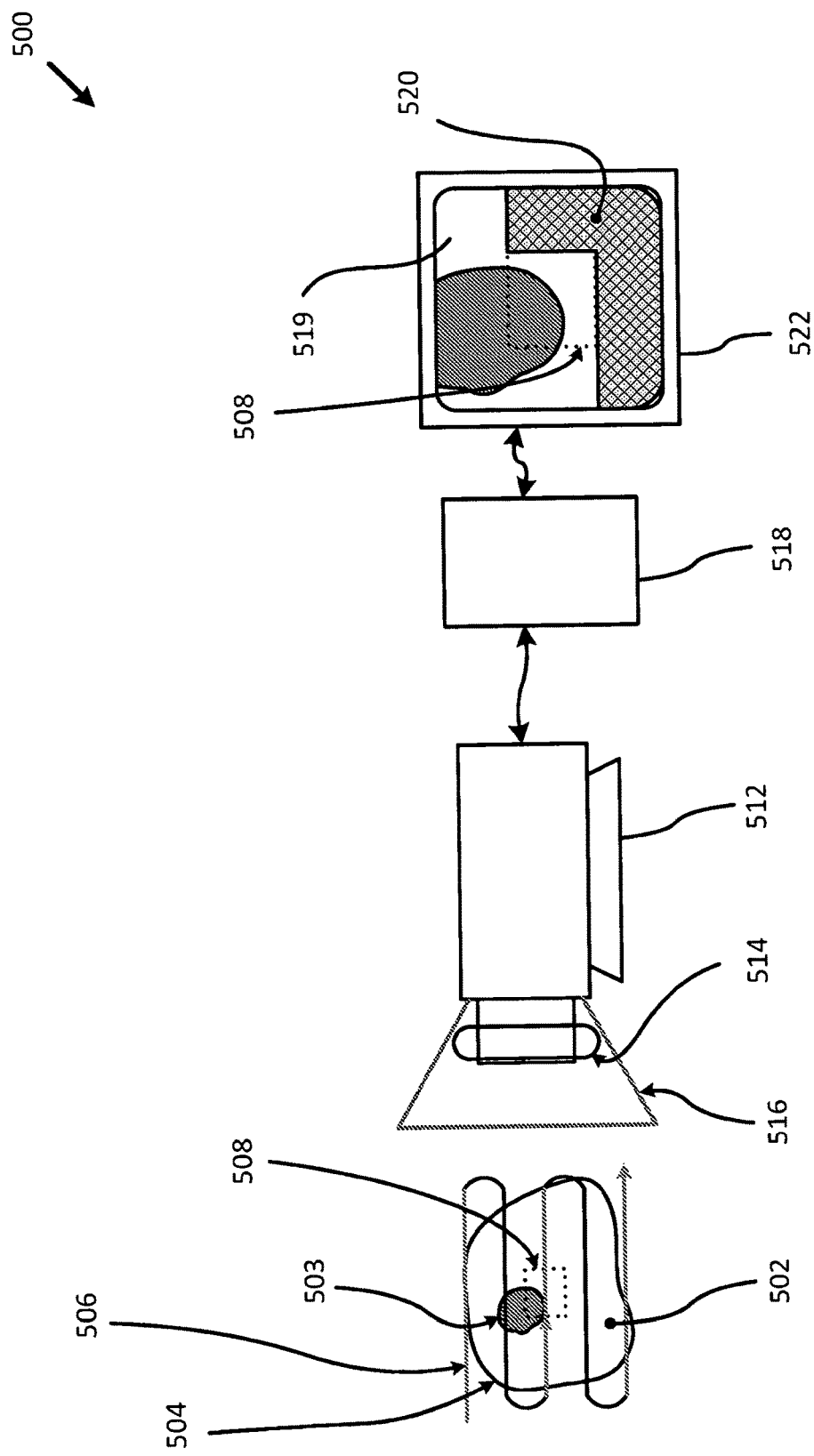
FIG. 6 illustrates another example skin feature imaging system.

The device 102 includes a camera 103 and a skin feature monitoring engine 105. Although not shown in FIG. 1, the device 102 includes components of a computing device, such as those shown in FIG. 9, which is described in more detail below. In embodiments, device 102 is a handheld device, such as a smart phone, tablet computing device, digital camera, or a specialized device as shown in FIGS. 6-7.

The skin feature monitoring engine 105 may reside in device 102, server 108, or be distributed between the device 102 and server 108. In embodiments, the skin feature monitoring engine 105 may operate over distributed systems (e.g., cloud-based computing systems), where application functionality, memory, data storage and retrieval and various processing functions may be operated remotely from each other over a distributed computing network, such as the Internet or an intranet. In distributed processing embodiments, the skin feature monitoring engine 105 on device 102 may have different sensitivity and specificity than skin feature monitoring engine 105 on server 108. This architecture allows the system to do more or less analysis based on computation power and available memory. For example, device 102 may have less processing power than server 108, so device 102 may be configured for high sensitivity, low specificity (likely to detect all true positives and also likely to have false positives) so that it operates as a screening algorithm, while the server 108 runs a more computationally intensive algorithm with improved specificity and sensitivity.

Generally, the skin feature monitoring engine 105 operates to, for example, guide the image capture of the patient's P skin, analyze the captured images, and present the images and analysis to the medical professional MP. The skin feature monitoring engine 105 can also provide reminders to the patient P about updating the images via one or more of the notification systems of the device 102. The system may also make notifications based on a comparison of events, for example, by noting an imaging date was scheduled but no new images have been uploaded to the database. Non-limiting examples of notification methods include text messages, e-mail messages, phone calls, voice mail, calendar entries, and other electronics solutions. Messages may be delivered to various electronic devices such as smart phones, smart TVs, automobile communication systems, smart watches, and the like.

The device 102 is in communication with the server 108 via network 106. Network 106 may be any type of wired or wireless network, for example, the Internet, an intranet, a wide area network (WAN), a local area network (LAN), and a virtual private network (VPN). It may also include short-range connections such as USB, Bluetooth, Bluetooth Low Energy, ZigBee, Ant, and the like. In embodiments, the server 108 has access to the patient's P electronic medical record (EMR) and/or electronic health record (EHR). Device 102 may also have access to the patient's P EMR/EHR. Providing documents to a clinician may be accomplished by sending the documents to an EMR/EHR, by e-mail, by upload to a server, or other electronic means. It may also include having the patient download the images and then the patient provides the images to the doctor.

Database 112 may store current and prior images as well as additional data such as the date, time, patient name, diagnoses, fiducials, body area, body maps, diagnoses, lab results such as biopsy reports, lists of moles the doctor selected for additional evaluation and the like. A biopsy report and a doctor's clinical assessment may be included as clinical results in the database as part of the metadata that provides details of various aspects of the image. Patient history, prescriptions, prior procedures, diagnoses, lab results, and other medically relevant information may also be included in the database and considered in the analysis and update of the skin feature monitoring engine algorithms, including weighting factors. For example, during pregnancy, it is common for moles to change evenly due to hormonal changes. They may become darker or larger and remain benign; however, uneven and/or irregular changes may indicate a malignant condition. Moles also darken after exposure to the sun and during the teen years. The algorithm would more likely consider "normal" the darkening of moles in a woman who is pregnant; a patient whose overall skin color is darker (sun exposure) and a teen-age patient.

Database 112 may reside in the server 108 or on a separate computing device accessible by the server 108 and/or the device 102. Database 112 may contain de-identified data such as image, encrypted electronic protected health information (ePHI), or coded patient data. Coded patient data removes all ePHI and replaces it with a code that cannot be connected to the remaining, non-protected health information. A lookup table, optionally located at the medical professional's office, allows a medical professional to pair the ePHI with the other non-protected patient data, such as the images. Database 112 may be instantiated in an EHR/EMR and/or a secure, HIPAA-compliant storage solution such as BOX from Box.com.

Monitor 110 displays the images of the patient's P skin features to the medical professional MP. Monitor 110 is in communication with server 108 either via a wired connection or wirelessly. In embodiments, monitor 110 is a handheld computing device (including cellular phones, tablets and the like), a laptop computing device, and/or a desktop monitor.

Figure 2:
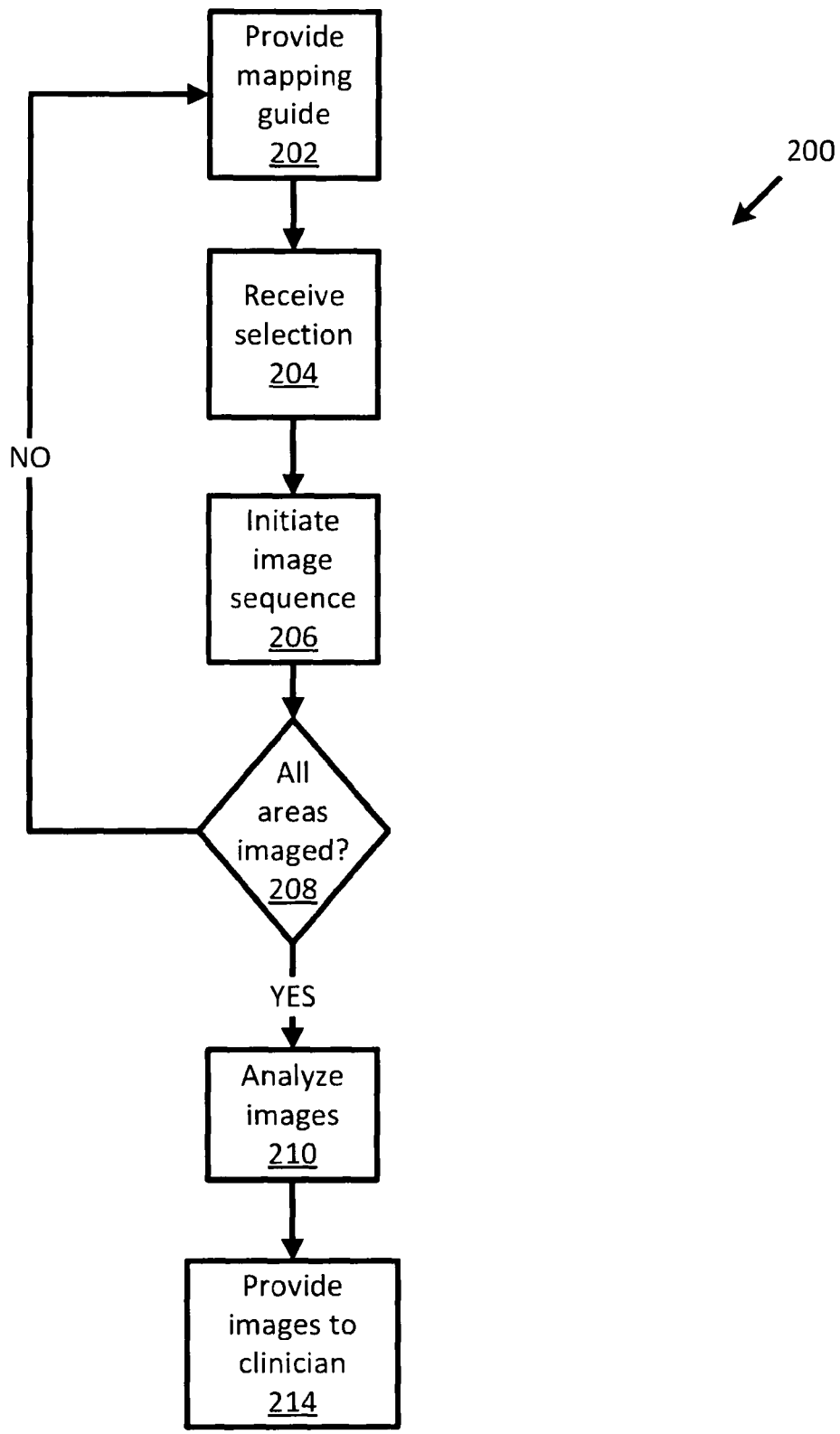
FIG. 2 illustrates an example method for monitoring skin features.

FIG. 2 illustrates an embodiment of an example method 200 for generating a series of skin images using the skin feature imaging system 100. The example method 200 includes providing a mapping guide (operation 202), receiving a selection (operation 204), initiating an image sequence (operation 206), determining whether all areas are captured (operation 208), analyzing images (operation 210), and providing images to the clinician (operation 214). The example method 200 is performed by the example skin feature monitoring engine 105 hosted by device 102 described above with reference to FIG. 1. Generally, the example method 200 begins after a device user initiates the skin feature monitoring engine, such as when a user selects an application running on the device. The device user may be the patient, a friend or family member of the patient, or a clinician. Other embodiments can include more or fewer operations.

The example method 200 begins by providing a mapping guide (operation 202). The mapping guide is a schematic depiction of a human body, divided into a plurality of body area sections for all sides (e.g., back, front, left, right, top (of head), and bottom (of feet)) of the human body. The ensemble of the various body sections is a body area guide. Each section may be highlighted, as with a contrasting color, to provide the user with an indication of what part of the body it being imaged and/or examined. The system may select the section to be imaged based on various parameters, such as history or mole risk index. The user may select a particular section, for example, by tapping on a particular area. Allowance is provided for the system to enlarge the image and also to divide a body area into smaller areas to support finer resolution mapping. The system may automatically detect the output display and provide different body area guides based on the display size and resolution. For example, on a 24-inch display, the entire body area guide for the front, back, both sides, feet, and head might be displayed. On a 10-inch display, one area, such as the front, might be displayed. On a smartphone-sized display of 5 inches, a section of the front of the body might be displayed. In one embodiment, once a body area has been selected the system determines what skin features are in that area and indicates these on the selected the body area section, initiating an image sequence of the body area. The body area guide can be dynamic. For example, a wide-angle view can indicate only portions of the anatomy that have skin features of concern. For example, for a patient with only one suspect skin feature on the arm, then the body area guide can only include that arm. Indications may include prior images of skin features to show the user the shape, size and color of the skin to aid in identifying the correct skin feature to image. The specific area to image may be a single skin feature. Differently-shaped schematic depictions of the human body may be used, for example, for male and female and for pediatric and adult.

The depiction of the front of the human body includes sections with generally equal surface areas. In embodiments, the front of the human body includes anywhere from 5 sections to 30 sections or more, with all numbers between 5 and 30 included. The depiction of the back of the human body has a similar configuration, with roughly congruent section sizes and from 5 sections to 30 sections or more.

Each body area shown in the mapping guide is user-selectable. Each section can display whether any images have been taken of that section previously, as well as whether any skin features have been previously identified in that region.

In embodiments, providing the mapping guide (operation 202) includes displaying information, options, and/or body areas based on learning from prior sessions or from a larger database including biopsy results. For example, if the medical professional selected a subset of moles for detailed examination, and/or noted a subset of moles to watch, and this subset of moles is indicated in the database, the selection may guide the user to image these moles more often than others.

After providing the mapping guide (operation 202), a user selection is received (operation 204). The user selection is of a particular body area. By choosing one of the user-selectable body areas, the user indicates that they want to photograph and begin tracking one or more skin features located within that body area. Alternately, the user can be guided through different selections.

Receiving a body area selection (operation 204) causes the initiation of an image sequence (operation 206). The image sequence includes providing on-screen guidance to the user and capturing one or more skin feature images. The images are captured using the device's camera. In embodiments where the device includes a flash, the images may be captured during flash illumination. Additional operations that are included in the image sequence (operation 206) are shown and described with reference to FIG. 3, below. Several captured images from a specific area may be compared with one another and with body fiducials such as, for example, the naval, knee, and elbow, to help verify which mole from the area was imaged. The system may connect all the images of a given skin feature. For example, skin features in the database may each have a unique ID and every image of that skin feature contains that unique ID.

Image sequences may be automated. As an example, a camera supports software control of zoom and focus. The user can be prompted to move so that a certain body section is toward the camera. The software detects when the appropriate area is in the field of view, instructs the user to stop moving, focuses the lens, and takes the image. Software can select to optically zoom in on specific skin features for higher resolution images.

In another implementation, the user can take "selfies" with a twist. Instead of awkwardly holding the camera, the user (the patient) uses a hand-held device such as a cellular phone to connect to the camera. This allows the user to see and control the camera remotely while being able to see what the camera sees. In this way, the user can, for example, have his back to the camera and see an image of his back. When framed correctly, the user (or system software) can record an image. Similarly, the user can control the focus and zoom via the application to zoom in on any suspect areas he/she may want imaged for clinical review. The body map can be scaled to match the user's size and super-imposed on the real-time image of the user.

After capturing images of the selected body area (operation 206), there is a check whether all body areas have been imaged (operation 208). In some embodiments, the system verifies that a new image has been obtained for each unique ID in the system. The system may further compare the new image to prior images to verify that the correct skin feature has been imaged. After this verification, the system may add the unique ID to the image's metadata.

In some embodiments, the skin feature monitoring engine prompts the patient about whether there are additional body areas to be imaged. In embodiments where the user or historical data has indicated there are skin features in other body areas, the skin feature monitoring engine can check whether each of those skin features have been imaged. If additional images are required, the example method 200 returns to providing the mapping guide (operation 202). If all images have been captured, then the example method 200 continues to analyze the images (operation 210).

If the example method 200 returns to providing the mapping guide (operation 202), then the mapping guide additionally includes one or more indications showing where images have been taken. In embodiments, the mapping guide can additionally include one or more indications showing where the user should capture more images.

After determining that no more body areas require imaging, the images are analyzed (operation 210). Analyzing the images includes producing a risk ranking for each skin feature and/or each image. Additional details and operations included in analyzing images (operation 210) are shown and described below with reference to FIG. 4. Analysis results may be added to the image metadata. These data may be stored as part of the image, for example in a .jpg image header, in a database, for example as fields in a record, or using other logical means to identify the data as linked together.

Next, the clinician accesses the images (operation 214) and conducts their own analysis. In embodiments, the clinician is presented skin feature images in the order of highest risk to lowest risk. Ranking the images is shown and described in more detail below with reference to FIG. 4. By presenting the images in this order, the system attempts to ensure that the clinician views the riskiest skin features before any decline in attention or focus by the clinician. In other embodiments, the clinician can select body areas to view the images captured of the skin features therein. In yet other embodiments, the system presents skin-feature guidance messages to the patient and/or the clinician. Example guidance might include, "Schedule an appointment with your dermatologist," "A skin feature has shown significant change since the prior image," or "Some skin features should be imaged more often," or a listing of the skin features presenting the highest risk.

Figure 3:
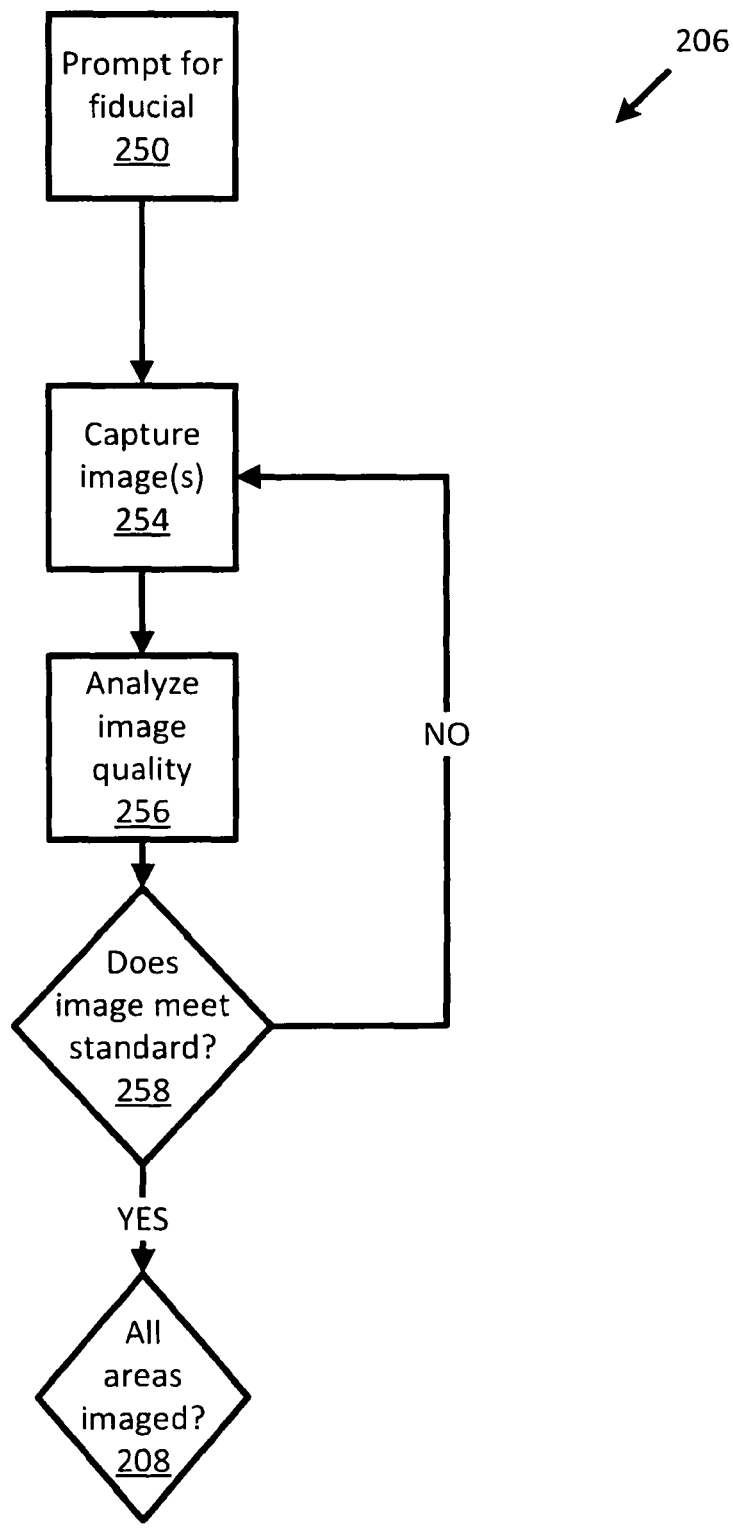
FIG. 3 illustrates an example method for an imaging sequence.

FIG. 3 illustrates an embodiment of the example imaging sequence (operation 206), which is part of the example method 200 for skin feature imaging. Initiating the image sequence (operation 206) includes prompting for a fiducial (operation 250), capturing one or more images (operation 254), analyzing the image quality (operation 256), and determining whether the images meet a standard (decision 258). Other embodiments can include more or fewer operations.

The example image sequence (operation 206) begins by prompting for a fiducial (operation 250). In embodiments, the fiducial is a physical item that is placed on or around the skin feature. For example, the fiducial is a circular sheet of paper with adhesive on one side and a bar code, Quick Response (QR) code, or other type of machine-readable code printed on the opposite side. The fiducial may include one or more other markers used by the device during image capture and/or post-processing. A different fiducial with a unique code may be used for each skin feature during a given imaging session.

A fiducial may also be a mark such as a circle that the physician writes on the skin indicating a skin feature to be imaged. Given an image of the entire body or body section, image processing software can analyze the image to detect skin features either by detecting the fiducials and/or by detecting skin features as part of generating a guide and indicating a specific area to image and determining if all the skin features in a body area have been imaged. Skin features may be detected using algorithms that look for specific aspects of skin features of interest such as color, edges, size and the like. These feature detection algorithms are conceptually similar to face, mouth, hair, and eye detection algorithms known to those skilled in the art.

The fiducial can be of a known size, which can be used later during image processing to determine the size of the skin feature. The known size may be encoded on the surface of the fiducial, for example, using a bar code, using a particular pattern for each size, or simply by putting the text size on the top surface of the fiducial. In embodiments where the fiducial includes markers, one or more of the markers can be used during image capture to focus the camera. Additionally, one or more of the markers can be used during analyzing the images (operation 210) to locate each skin feature and/or to calibrate color.

Color calibration (also known as color correction) is beneficial because the imaged color of a skin feature is dependent on the lighting, and differential images of the same skin feature on the same day but with different lighting would indicate a false color evolution. Similarly, if the skin feature changes color in a given direction, say red, and the lighting changes away from red, the skin feature color change would be less detectable in a differential measurement without color correction. Change in skin color, such as from tanning, also affects the color balance of the image and hence the recorded color of the skin feature. Color calibration methods are known to those skilled in the art. Example color calibration methods can be implemented by: use of a background light sensor, taking a picture of a calibrated color chart, and/or taking a picture of a white or neutral grey image.

The code on the fiducial may be associated with the patient. The code on the fiducial may be a unique ID associated with that skin feature. Other methods may be used to determine the size of the skin feature. For example, given the focal length of the lens, the size of the imaging sensor, the number of pixels in the x- and y-directions and the focus distance, the actual size of the mole may be calculated. The size of the sensor and the number of pixels provides the pixel size. To determine the size of the feature in pixels, the real diameter is given by:

$$(object\_size\_in\_pixels * pixel\_size * focus\_distance) / (focal\_length).$$

In some embodiments, the fiducial is added to the image by the skin feature monitoring engine 105. The fiducial is either included as part of the image as a part of the image's metadata, for example, the using the Exif (exchangeable image file format) standard, or as a separate entry in a database. Standard elements of image metadata include focal length, F-stop, exposure time, ISO speed, exposure bias, metering mode, subject distance, flash mode, flash energy, 35 mm focal length, image dimensions in pixels, horizontal and vertical resolution in dots per inch, color bit depth, date, time, thumbnail image, GPS location and the like. These standard metadata elements are stored as part of the image by the camera when an image is created. Other metadata elements may be added to the image after it is created by the camera. Other metadata elements may be stored separately from the image, for example in a database. Metadata elements may be extracted from the image and stored as elements in a database or other storage system. If stored separately from the image, then a logical connection to the image may be used. For example, the separate metadata may include the image path and filename. In another embodiment, having the image and the metadata in the same record of a database would provide the logical connection. In embodiments, the notes in the image may include patient name, patient ID, a unique identifier for the skin feature, body area, focal distance, date, time, patient date of birth, and/or other information.

After prompting for a fiducial (operation 250), one or more images are captured (operation 254). In embodiments, for a given body area and/or identified skin feature, the camera captures a series of images at different focal lengths. By capturing a series of images while adjusting the focal point, at least some of the images should be properly focused on the patient's skin. In some instances, the camera's auto-focus will focus on the patient's body hair rather than the patient's skin. The focusing algorithm can detect when the focus is made on hair and feedback a correction, for example, indicating that the focus point should be slightly further away.

In embodiments, where a fiducial includes a marker to assist in focusing, the camera does not capture a series of images at different focal lengths. Instead, the camera focuses on the marker and, when properly focused on the marker, captures the image.

In embodiments, the patient is prompted to capture a first wide-angle image, which may be then digitally annotated for a given number of important areas. The important areas may be mapped onto the schematic depiction of the human body. Then the patient is prompted to take specific close-up shots within the wide-angle image.

In embodiments, the device includes RF, ultrasonic or optical ranging. The time between emitting the ranging signal and receiving the reflection of the signal from the patient's skin can be used to determine the distance of the camera from the patient's skin. In turn, using Geometric formulae, this known distance can be used to determine the size of the skin feature. Many cameras use phase detection or contrast detection for focus. Once focused, the camera determines the distance to the subject and this distance from the camera to the patient's skin may be included in the image metadata, which may be used during analyzing the images (operation 210). In various embodiments, pin-point autofocus, cross-type autofocus sensors, or continuous autofocus can be used.

When one or more images have been captured (operation 254), each image is analyzed for quality (operation 256). Analyzing image quality (operation 256) includes determining the quality of the focus and color.

Quality of focus and color may be assessed by using algorithms known to those skilled in the art. A specific addition to those algorithms is to provide to the focus algorithm and the color correction algorithm the subset of the image that is important. In cameras, there is often a focus "dot" the camera operator places over the important part of the image, for example. One method to determine if an image is in good focus is to assess the contrast, which is the scale of difference between black and white.

An example of an algorithm to assess focus quality can be described by considering an image that contains vertical black and white stripes, each 3 pixels wide and a total of 9 stripes. By comparing the average pixel value of each vertical column of pixels, it is expected to observe a result such as: 0, 0, 0, 255, 255, 255, 0, 0, 0, 255, 255, 255. The absolute value of change from one column to another would be: 0, 0, 255, 0, 0, 255, 0, 0, 255, 0, 0; the sum of these changes is 765 and this may be considered a contrast measure.

When an image is blurred, the black and white mix to a certain extent, resulting in fuzzy edges to the black stripes. Comparing the average pixel value of each vertical column of pixels, might reveal a result such as: 0, 0, 43, 128, 170, 128, 43, 0, 43, 128, 170, 128. The absolute value of change from one column to another would be: 0, 0, 43, 85, 42, 42, 85, 43, 43, 85, 42, 42 and the sum of these changes is 552.

Many auto-focusing systems only focus well when there is a strong vertical (or a strong horizontal) line. Software selects these vertical lines and the auto-focusing system changes the focus to maximize the contrast measure of image in the area of the vertical lines.

The instantly-disclosed system may select the fiducial or part of the fiducial, as the area on which to focus and determine if the focus is sharp. The system may be calibrated with a tested range of acceptable values for the contrast measure. The system may be designed to search for a mole or other skin feature, identify the edge of the mole and use contrast measures of the edge the mole to determine if the focus is sharp. Color may be adjusted using algorithms known to those in the art when the image is of a white or neutral grey background. These algorithms separate the image into RGB color space where, for white or neutral grey images, the red, green, and blue histograms will match under white light. If the light has a blue bias, then the value of the blue pixels exceeds that of the red and green pixels. An algorithm scales the red, green, and blue pixels to have values that match. In this case, when a subset of the image such as the fiducial contains neutral grey, the color adjustment algorithm includes a first step of selection the fiducial and extracting the RGB levels from the fiducial to make the adjustment.

Alternately, calibrated colors may be printed on the fiducial and the calibrated color values are provided to the algorithm. For example, the "red" might have RGB values of (100, 10, 10). Analysis of the "red" section of the image may show the section has an average RGB triplet of (120, 8, 8). That is, the image is redder than would be seen under white light. If the red pixels are multiplied by 100/120 and all green pixels are multiplied by 10/8 and all blue pixels are multiplied by 10/8, then the color-corrected image will have an average RGB triplet of (100, 10, 10). Other colors may be used. If the color is neutral grey, then the expected triplet might be (64, 64, 64), that is, all pixels have the same value. Scaling is not just finding the ratios, but also the comparison of the absolute values of the colors to the values of an image taken under known, good lighting conditions, thus allowing the system to ensure the brightness of the light is consistent across all the images as well as the color.

Additional analysis may include verification that none of the image is too dark and that none of the image is too light. A simple test for this is to evaluate the number of pixels in the area(s) of interest that are clipped. That is, having value 0 or camera's maximum (255 for 8-bits/color). The system can take images at multiple exposures to help ensure that at least one image is of appropriate exposure. The system can combine images of different exposures to achieve high dynamic range.

Additional analysis may evaluate the location of the histogram and ensure it is a "high key" image where most of the tones occur in the highlights. If the histogram indicates a "low key" image most of the tones occur in the shadows, then the signal-to-noise ratio may be compromised and there is more quantization noise because the number of bits available to represent the data is decreased as compared to a high key image. From multiple exposures of the same view, the system may select the image that is the "highest key" while avoiding any saturated pixels. Evaluating quality of focus may include determination that focus is on the wrong thing, for example on hair. Algorithms for detection of hair are known to those skilled in the art.

If the quality of the focus and color does not meet a standard (decision 258), the user is again prompted and/or guided to capture additional images of the skin features. In the case of automated image capture, the system may continue to acquire and analyze images of a body site until an acceptable image is captured. Alternatively, if the quality of the focus and color meets the standard, the example method 200 continues to determining whether all body areas have been imaged (operation 208), discussed in more detail above with reference to FIG. 2. By taking multiple images at slightly different focus points and at slightly different exposures, the system increases the probability that an acceptable image was made for each body section or skin feature imaged.

Figure 4:
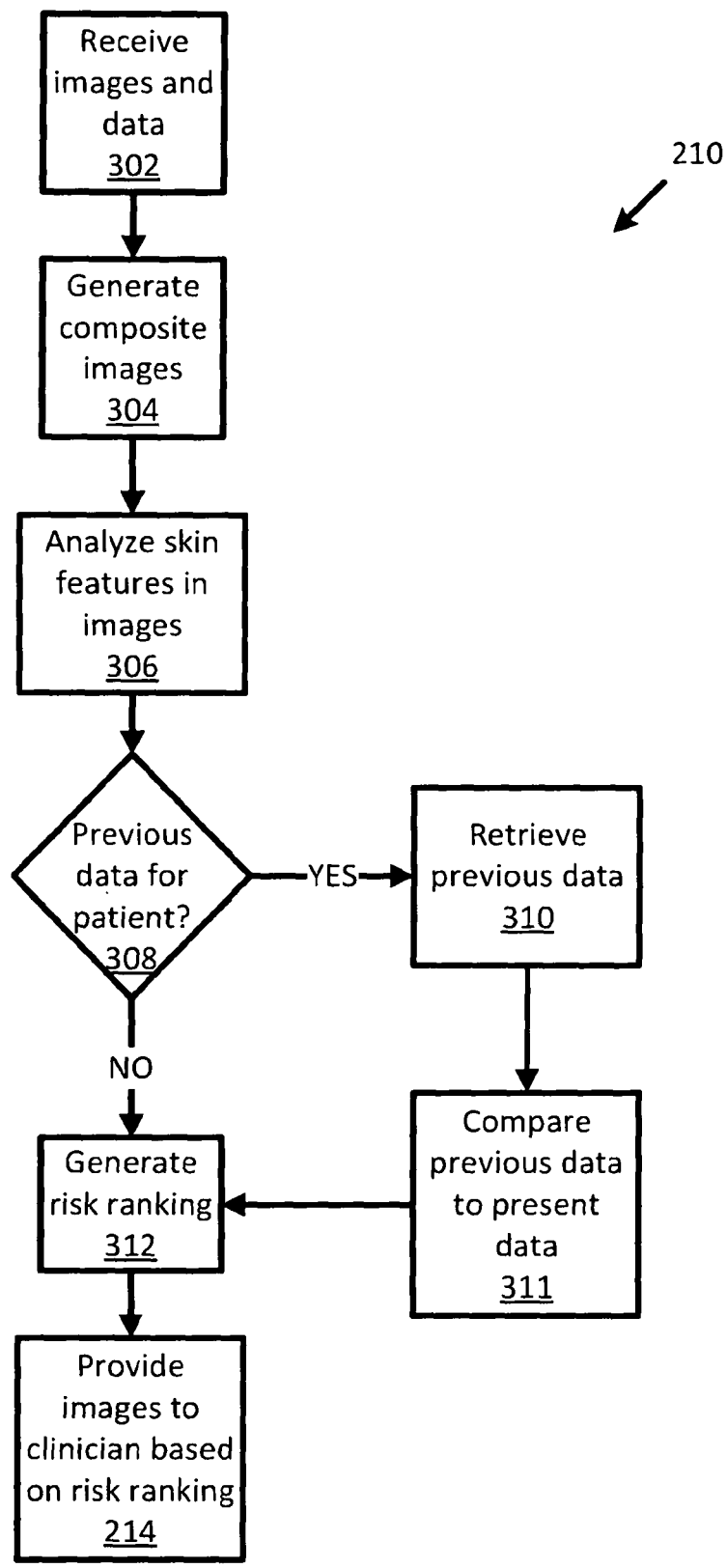
FIG. 4 illustrates an example method for analyzing images.

FIG. 4 illustrates an embodiment of analyzing images (operation 210), which is part of the example method 200 for skin feature imaging. Analyzing images (operation 210) includes receiving images and data (operation 302), generating composite images (operation 304), analyzing the skin features in the images (operation 306), determining whether there are previous data for the patient (operation 308), retrieving previous data (operation 310), comparing previous data to present data (operation 311), generating a risk ranking (operation 312), and providing images to the clinician based on the risk ranking (operation 214). In embodiments, the server 108, shown in FIG. 1, executes one or more of the operations shown in FIG. 4. In embodiments, the device 102 executes one or more of operations 304-312 shown in FIG. 4. Other embodiments can include more or fewer operations. Composite image methods are known to those skilled in the art and may be generated by combining multiple adjacent images into a larger image, by combining multispectral images, and/or by combining images of the same area with different exposures.

Analyzing images (operation 210) begins with receiving images and data (operation 302). The device 102 transmits the images, including any metadata and additional data associated with the patient and/or the skin features, via network 106 to the server 108 for analysis.

After receiving images and data (operation 302), composite images are generated (operation 304) using the received images. In embodiments, the device generates composite images in real-time as the images are captured. The fiducials used during image capture can aid in stitching together the captured images. In embodiments, the fiducials, either natural (part of the body, such as moles or hairs) or artificial may be used to stitch together the images. In embodiments where a zoomed-out image is first captured, that image can be linked to the composite images. Moreover, one or more of the zoomed-out images can be stitched together.

In embodiments, the device is used to capture video of the patient's skin. In those embodiments, operation 304 includes analyzing the video feed and stitching together a composite still image. The composite still image can include a wide-angle view, which the clinician can use for reference to landmarks, as well as macro views for detailed image inspection. Using an accelerometer, gyroscope, or similar motion detector, the system can determine the motion of the camera and use this as an aid in stitching. For example, if left-to-right motion stops and the camera begins moving down, the stitching algorithm knows to stop placing images side-by-side and to start placing the top of the next image below the top of the current image.

Next, the skin features in the images are analyzed (operation 306). Operation 306 includes correcting for color in the images. In embodiments with physical fiducials on the patient's skin, those fiducials can include color standards to calibrate the image processing. Additionally, the fiducials are used to provide a scale which is used to determine the size of the skin features.

In embodiments, analyzing skin features (operation 306) includes determining the "ABCDE" for every identified skin feature: Asymmetry, Border, Color, Diameter, and Evolving/Elevation. Evolving is discussed below with reference to operation 311. Other measures including, but not limited to those mentioned above, may be used for analyzing skin features For example, each skin feature is analyzed to determine a level of asymmetry. In embodiments, the centroid of the skin feature is first identified and then the color, border, and/or other features are compared for symmetry around the centroid.

The border is analyzed to determine a level of irregularity. In embodiments, the border is identified by determining a color or tonal transition between the skin feature and the skin. Then the identified border is compared to geometric shapes, such as circles, ovals, ellipses, etc. The amount or degree of notching, scalloping, or irregularity in the border is determined.

The color is analyzed to determine a degree of color variation across the skin feature. As mentioned above, the color can be compared and/or calibrated using a standard on a physical fiducial. A plurality of areas on the skin feature are selected, the color of the area determined, and then the areas are compared to the other areas in the skin feature. Thereby, any areas of the skin feature that have different coloration can be identified and rated.

One or more diameters of the skin feature are determined using the border identified earlier. Because many skin features are not perfectly circular, multiple diameters at different locations can be determined. Then, the largest diameter, or an average of the diameters, is used.

After, or as part of, analyzing the skin features in the captured images (operation 306), a determination is made whether there are previous data for the patient (operation 308). If the patient does not have any previous data, either stored locally or in the patient's EHR or EMR, then the operation 210 proceeds to generate a risk ranking for each skin feature (operation 312).

Analyzing skin features (operation 306) may include comparison to reference skin features in the database that are prior images from the patient and also reference skin features that are not from this patient, such as identifying moles that were excised and determined to be malignant. Reference skin features preferably maximize the number of common traits of both the skin feature and the patient.

If there are previous data for the patient, the previous data for the patient are retrieved (operation 310). In embodiments, the patient's data are stored locally on the device or server, in the patient's EHR or EMR, or in another database accessible to the device or server. The patient's data can be associated with the patient by medical ID, name, date of birth, social security number, or other identifiers.

Next, the skin features are correlated to the previously-captured and analyzed images and compared (operation 311). An embodiment of a determination of evolution is shown in FIG. 5, described in more detail below. During operation 311, the evolution of each skin feature is determined. For instance, changes in symmetry, border, color, and size are evaluated. The extent of each of these changes is used in rating each skin feature.

In embodiments, a database includes images for which a biopsy was positive for melanoma, as well as images for moles determined by medical professionals to be benign.

During analysis (operation 306), the skin feature monitoring engine compares a present image, or features of the image, to the database and, if a critical level of features match the database of moles biopsied for melanoma, then the patient and the medical professional are alerted and that mole is noted in the database, for example, as "suspect". This additional label enables later data analysis processes to quickly find all moles that are "suspect" for melanoma. Additionally, by obtaining time-series images of moles that progress to melanoma and the application of data analytics, the skin feature monitoring engine learns and improves its ability to more quickly and/or more accurately flag "suspect" moles.

The time-series images allow the system to present the evolution of the skin feature to a clinician. As an example, if there are six images and the first four images are virtually identical, but the $5^{th}$ and $6^{th}$ differ from each other and from image 4, then the system may present images 4, 5, 6 for the clinician to review. The system may present for review the differential images of image4 to image5, image5 to image6, and/or image4 to image 6. The system may provide a risk metric that defines the amount of risk above which time-series images and/or differential images are automatically displayed. A time-series of differential images may be displayed, for example, the difference from the $4^{th}$ to $5^{th}$ and from the $5^{th}$ to $6^{th}$ image. The system may allow the clinician to select a set of images from which differential and/or time-series display is created and displayed. For example, the clinician may choose to examine the differential image showing the change from the $4^{th}$ to the $6^{th}$ image. A risk ranking may be presented separate from or alongside the images. Similarly, moles that are identified by a medical professional as benign may be flagged so the mapping guide requests imaging of those moles less often.

The skin feature monitoring engine may create rules, for example classification rules, that are updated as more images, image features, biopsy results, clinical determinations, image update recommendations, patient observation and the like are added to the database. Patient observations might include comments such as bleeding, oozing, flaking, itchiness, pain, tenderness and the like. These classification rules are an example of how the skin feature monitoring engine might compare aspects and characteristics of a newly imaged skin feature to correlated aspects and characteristics of previously imaged skin features. Other methods exist for classifying aspects and characteristics.

As an example, different weighting factors may be applied to an aspect of a skin feature where the value of the weighting factor depends on how often skin features with certain aspects were found to be malignant vs benign. As an example, there is a general rule that if the diameter exceeds 6 mm, the mole is likely to be malignant. However, for some moles this rule isn't accurate. As an example, moles that are nearly perfectly round are almost never malignant. If a mole is 7 mm in diameter, it might have a diameter weighting of 10, but being perfectly round, the shape weighing is 0.1. The multiplied weighting is 1.0, indicating this mole has no elevated risk, despite the 7 mm diameter. Weighting factors may be updated as new data are received, for example, a biopsied mole with result "malignant" that the algorithm suspected was malignant would enforce the current algorithm while a biopsied mole with results "malignant" that the algorithm suspected was benign would tend to change the algorithm and/or weightings for features of that biopsied mole and the features of the patient. Patient-specific algorithms can be developed for patients with a large enough number of moles to provide a relevant sample.

In embodiments, the clinician is provided with one or more previous images of a given skin feature. Thereby, the clinician can observe the progression and development of the particular skin feature.

After each skin feature has been analyzed (operation 306), and, where applicable, the evolution of the skin feature determined (operation 311), a risk ranking is generated (operation 312). The risk ranking is used to determine the highest-risk skin features and to show those to the clinician first. The risk ranking may be determined by summing up the ratings for symmetry, border, color, size, and evolution. Other methods are possible. The term risk ranking may include any computer-generated risk, severity, or probability index that is used as an indication that guides diagnosis or treatment of skin features.

In embodiments, if a user had a skin feature that was previously highly rated, but no images were captured of that skin feature in the present imaging session, that area or skin feature can be highlighted to the clinician to follow up with the patient.

Figure 5A:
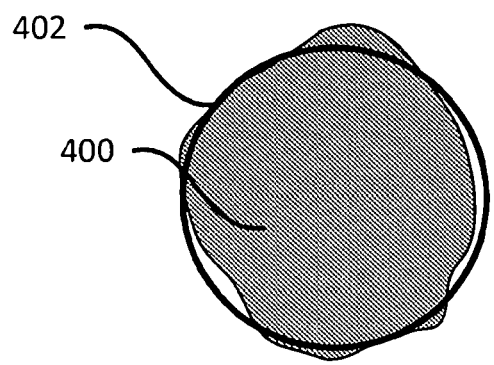
FIGS. 5A-5C illustrate an example method for determining of an evolution of one aspect of a skin feature.
Figure 5B:
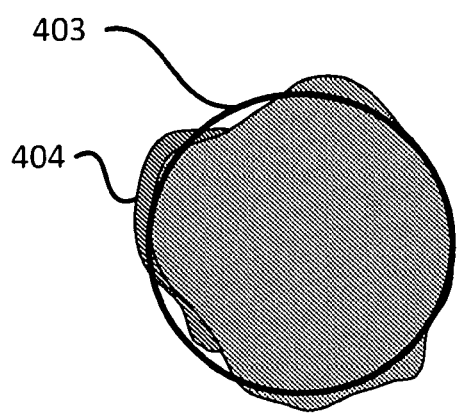
Figure 5C:
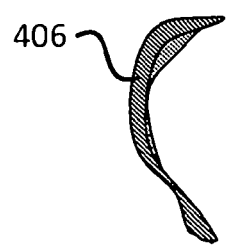

FIGS. 5A-5C illustrate an example method of determining the evolution of one aspect of a skin feature. The skin feature was imaged and processed with the skin feature monitoring engine, an example embodiment of which is shown in FIG. 1 and described in more detail above.

FIG. 5A is an image of a skin feature, in this instance, a mole 400 with a best fit circle 402. The best fit circle 402 approximates the border and size of the mole.

FIG. 5B is an image of the same mole 404 shown in FIG. 5A at a later time. A new best fit circle 403 is shown. For comparison purposes, the same best fit circle 402 from the earlier-imaged mole may be shown. In other embodiments, a new best-fit circle may be determined and the two different best fit circles compared.

FIG. 5C shows the calculated difference 406 between the current and previous images. In embodiments, the calculated difference 406 includes changes in coloration as well as size. In embodiments, the clinician is presented with the three images showing the progression of the mole, as well as what has been determined to be the changes over time. Regardless of any change detected by the skin feature monitoring engine, the system allows the patient P and the medical professional MP to scroll through images of each mole, such as in order by date of the image. Multiple methods may be available for the user to select a mole or set of moles. The user may follow the system-presented order ranked by risk. Alternately, the user may click on an area of the schematic depiction of the body and from there to a specific point that has a marker indicating that it matches the location of a mole.

FIG. 6 is a schematic, environmental view of another example skin feature monitoring system 500. FIG. 6 shows a patient's skin 502 having a skin feature 503 within a skin area to be scanned 504. An imaging device 512 with a current field of view 508 follows a scanning path 506. The imaging device 512 may include an annular light source 514 and a hood 516. The annular light source 514 may be polarized.

The imaging device 512 is in communication with a computing device 518. The computing device 518 provides real-time stitching of the images captured by the imaging device 512 and outputs the stitched image to a monitor 522. The view in the monitor 522 includes the scanned area 519, the camera's current field of view 508, and the unscanned area 520. Other embodiments can include more or fewer components.

The system may create the equivalent of a wide-angle view from the stitched image and it may automatically mark and identify skin features based on algorithms such as edge detection. The user may subsequently indicate if the areas are of interest or not. The scanning and stitching method may be any handheld device, such as a smart phone, tablet computing device, digital camera, or a specialized device as shown in FIGS. 6-7 may be used as the source in the scanning and stitching method. Because images are taken of the skin feature 503 from various angles, an estimate of the height (elevation) of the skin feature may be made through the use of parallax, as is used in aerial photography to measure heights of objects following the equation: Ho=Hc*Pd/(Pa+Pd), where Ho is the object height, He is the camera height above the object, Pd is the differential parallax and Pa is the absolute parallax. Using side lighting, the size of the shadow can be used to determine the objects height using the equation: Ho=Ls*tan($\alpha$), where $\alpha$ is the angle of the light source measured from the skin surface.

In embodiments, a health care professional or the patient uses the imaging device 512 to capture images of the patient's skin 502. The health care professional, patient, or other person conducting the scanning may first indicate the particular body area 504 that will be scanned, similar to the body area selection described above. For large enough areas or areas that contain a body fiducial such as the naval, sternal notch or the like, the system may automatically determine the body area.

Generally, the imaging device 512 includes a camera, camera lens, housing, and computing hardware, such as the computing components shown and described with reference to FIG. 9. As examples, the imaging device 512 is a web camera, smart phone, tablet computing device, or digital camera.

In the embodiment shown, the imaging device 512 includes a hood 516 with annular light source 514. The annular light source 514 is positioned circumferentially around a camera lens of the imaging device 512 for uniform lighting. For the purposes of estimating height, part of the light source can be disabled, resulting in an off-axis light source that creates a shadow, the size of which may be used to estimate the height of the mole. The hood 516 enables the imaging device 512 to be positioned against the patient's skin 502 a predetermined distance from the lens. In embodiments, hood 516 includes a polarization lens. Other embodiments may provide a polarized light source and the polarization angle may be adjustable. Other embodiments of imaging device 512 are shown and described with reference to FIGS. 7A-7B.

The imaging device 512 is moved across the patient's skin 502 in a pattern, such as example scanning path 506. During image capture, the computing device 518 provides real-time stitching of the captured images. The images may be still images or video images. The system can optimize the image acquisition rate to allow successful stitching while not requiring storage of an enormous number of images.

The person scanning the patient's skin 502 can view the real-time, scanned area 519 in monitor 522. The view in monitor 522 also shows the camera's current field of view 508 for reference. In embodiments, the view in monitor 522 may also show as any remaining unscanned area 520 in the selected body area, which can help guide the user in scanning the patient's skin.

Figure 7A:
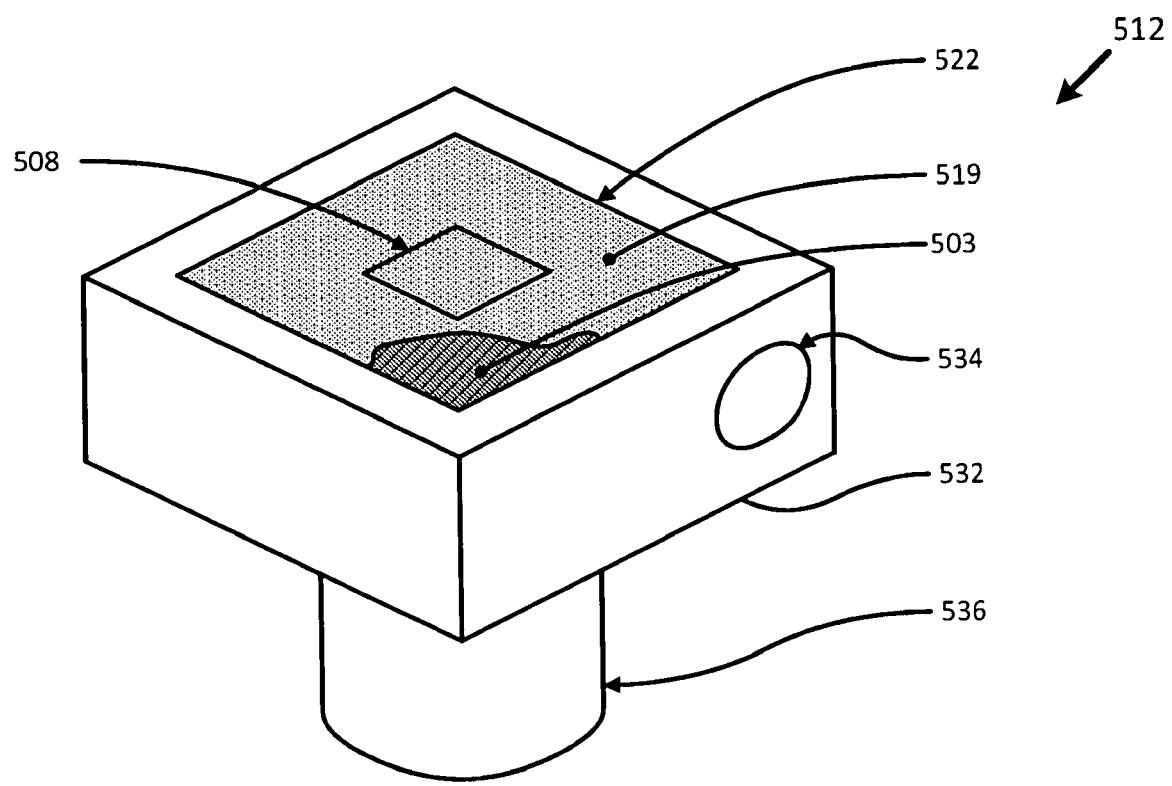
FIG. 7A illustrates a front isometric view of a second embodiment of an imaging device shown in FIG. 6.
Figure 7B:
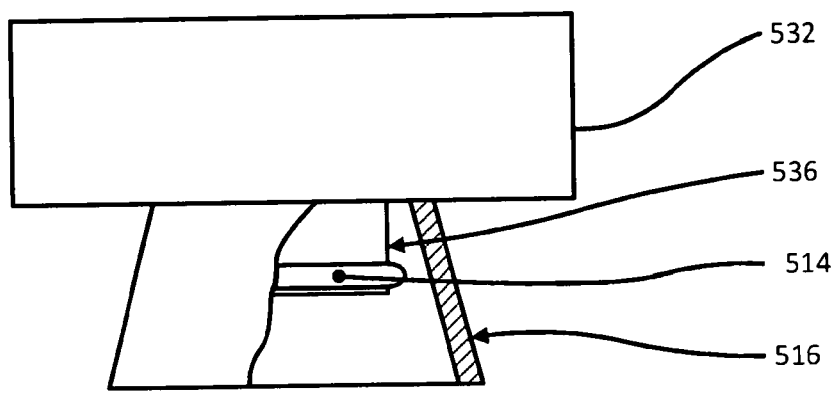
FIG. 7B illustrates a side sectional view of a third embodiment of an imaging device shown in FIG. 6.

FIG. 7A is a front isometric view of a second embodiment of the example imaging device 512. In the embodiment shown, the imaging device housing 532 also supports the computing device 518 and monitor 522. The second embodiment includes an image capture button 534, which can be used to initiate still image or video image capture. FIG. 7B also shows camera lens 536. The second embodiment does not include the optional hood 516 or the annular light source 514. Other embodiments may automatically capture an image when a mole or other skin feature is detected.

FIG. 7B is a side sectional view of a third embodiment of the example imaging device 512. The third embodiment includes all the components of the second embodiment, shown in FIG. 7A, and additionally includes hood 516 and annular light source 514.

Figure 8:
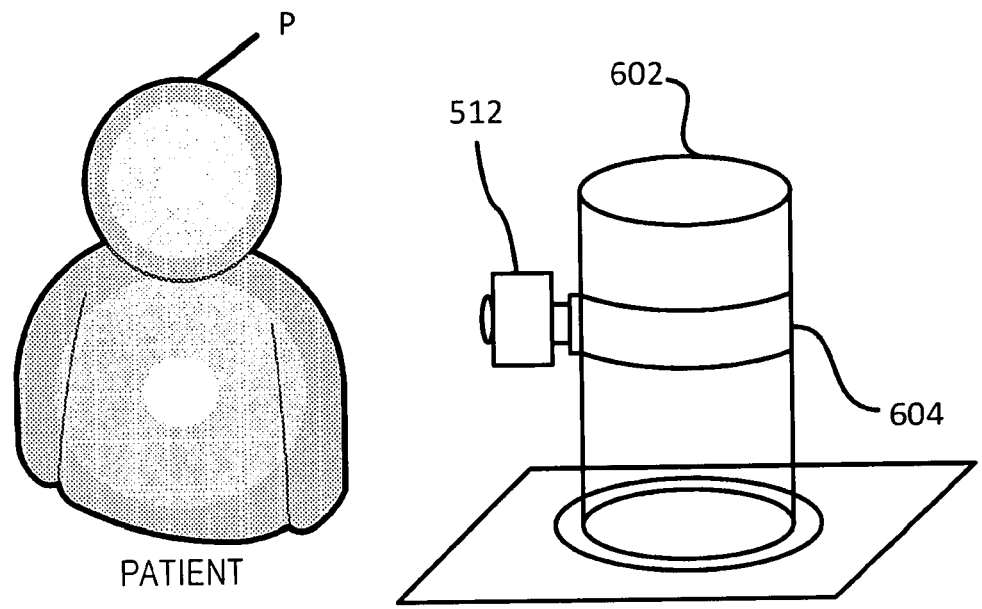
FIG. 8 illustrates a fourth embodiment of an imaging device shown in FIG. 6.

FIG. 8 is a schematic illustration of a fourth embodiment of the example imaging device 512 as supported by an elongated pole 602. A connector 604 supports the imaging device 512 and is movably attached to the elongated pole 602. The example imaging device 512 is movable in a vertical direction manually or automatically via connector 604. As the imaging device 512 captures images, and moves in the vertical direction, the patient is gradually rotated in place (or asked to rotate) such that a plurality of body areas are imaged.

Figure 9:
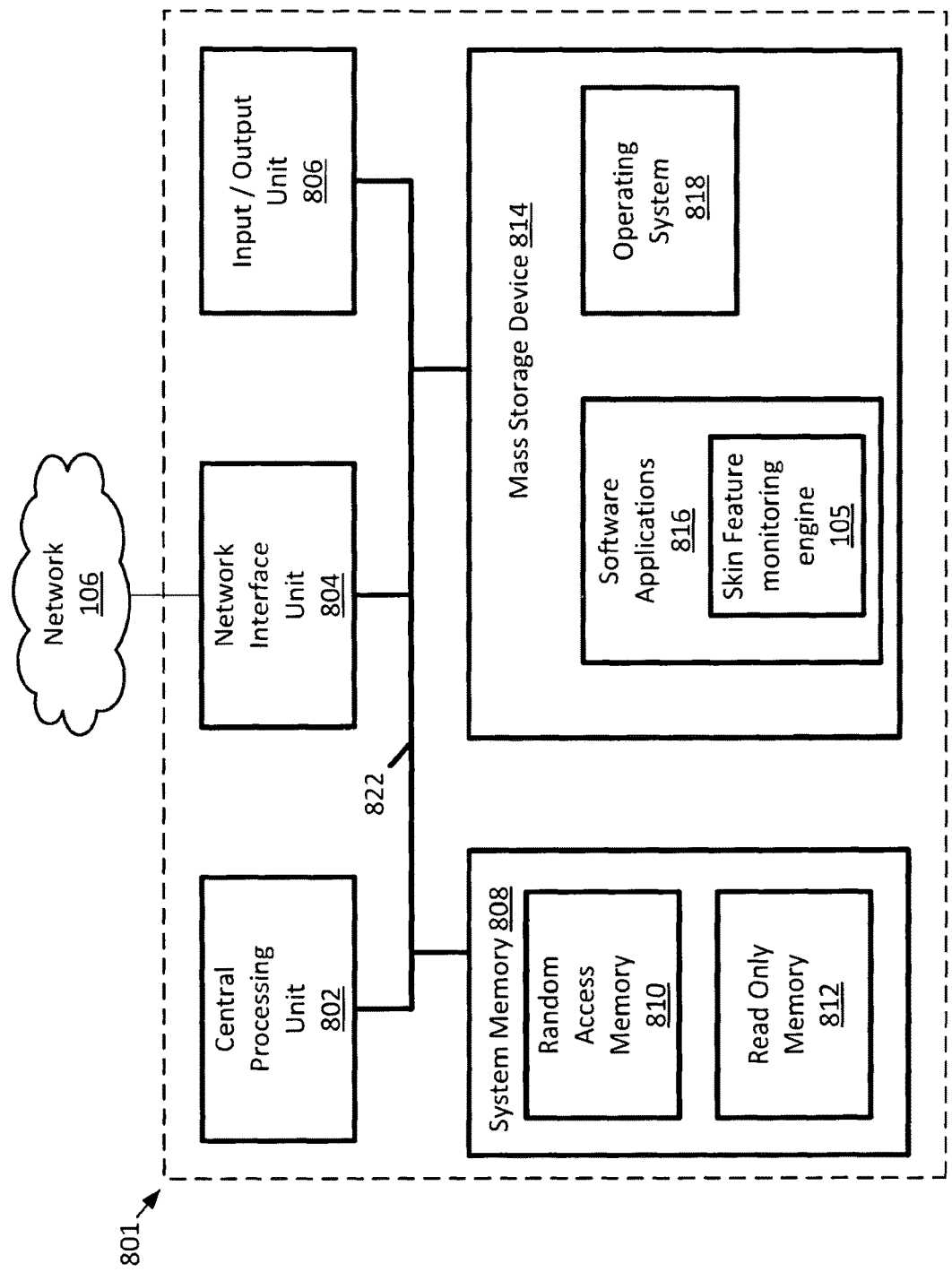
FIG. 9 illustrates an example computing unit used in the example skin feature imaging system.

FIG. 9 shows example computing components that can be incorporated as part of the device 102. As illustrated, the example computing device 801 includes at least one central processing unit ("CPU") 802, a system memory 808, and a system bus 822 that couples the system memory 808 to the CPU 802. The system memory 808 includes a random access memory ("RAM") 810 and a read-only memory ("ROM") 812. A basic input/output system that contains the basic routines that help to transfer information between elements within the example computing device 801, such as during startup, is stored in the ROM 812. The example computing device 801 further includes a mass storage device 814. The mass storage device 814 is able to store software instructions and data.

The mass storage device 814 is connected to the CPU 802 through a mass storage controller (not shown) connected to the system bus 822. The mass storage device 814 and its associated computer-readable data storage media provide non-volatile, non-transitory storage for the example computing device 801. Although the description of computer-readable data storage media contained herein refers to a mass storage device, such as a hard disk or solid state disk, it should be appreciated by those skilled in the art that computer-readable data storage media can be any available non-transitory, physical device or article of manufacture from which the central display station can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the example computing device 801.

According to various embodiments of the inventions, the example computing device 801 may operate in a networked environment using logical connections to remote network devices through the network 106, such as a wireless network, the Internet, or another type of network. The example computing device 801 may connect to the network 106 through a network interface unit 804 connected to the system bus 822. It should be appreciated that the network interface unit 804 may also be utilized to connect to other types of networks and remote computing systems. The example computing device 801 also includes an input/output controller 806 for receiving and processing input from a number of other devices, including a touch user interface display screen, or another type of input device. Similarly, the input/output controller 806 may provide output to a touch user interface display screen or other type of output device.

As mentioned briefly above, the mass storage device 814 and the RAM 810 of the example computing device 801 can store software instructions and data. The software instructions include an operating system 818 suitable for controlling the operation of the example computing device 801. The mass storage device 814 and/or the RAM 810 also store software applications 816, that when executed by the CPU 802, cause the example computing device 801 to provide the functionality of the example computing device 801 discussed in this document. For example, the mass storage device 814 and/or the RAM 810 can store software instructions that, when executed by the CPU 802, cause the example computing device 801 to display received data on the display screen of the example computing device 801.

The description and illustration of one or more embodiments provided in this application are not intended to limit or restrict the scope of the inventions as claimed in any way. The embodiments, examples, and details provided in this application are considered sufficient to convey possession and enable others to make and use the best mode of claimed inventions. The claimed inventions should not be construed as being limited to any embodiment, example, or detail provided in this application. Regardless whether shown and described in combination or separately, the various features (both structural and methodological) are intended to be selectively included or omitted to produce an embodiment with a particular set of features. Having been provided with the description and illustration of the present application, one skilled in the art may envision variations, modifications, and alternate embodiments falling within the spirit of the broader aspects of the claimed inventions and the general inventive concept embodied in this application that do not depart from the broader scope.

The invention claimed is:

1. A skin feature review system, comprising:
at least one processor;
a database storing previous data of a plurality of skin features of a patient, wherein the previous data include a reference image of each of the plurality of skin features and metadata, the metadata including an analysis of at least one characteristic of the skin features; and
memory comprising computer-executable instructions that, when executed by the at least one processor, cause the at least one processor to:
receive images of the plurality of skin features;
analyze the images of the plurality of skin features by comparing the images to the reference images included in the database;
provide one or more results of the analysis, wherein the one or more results of the analysis include at least a risk ranking;
use the risk ranking to determine a highest-risk skin feature; and
generate, based on the risk ranking, a listing of the plurality of skin features in order of the highest-risk skin feature to lowest risk.

2. The system of claim 1, wherein the results include differential images displayed based on the risk ranking.

3. The system of claim 1, wherein the results include time evolution images displayed based on a user selection.

4. The system of claim 1, wherein the risk ranking is generated based on ratings for symmetry, border, color, size, and evolution.

5. The system of claim 1, wherein the results include an image of a skin feature for which there is a reference image.

6. The system of claim 5, wherein the skin feature for which there is the reference image has been biopsied.

7. The system of claim 5, wherein the memory further encodes computer executable instructions that, when executed by the at least one processor, cause the at least one processor to:
receive a clinical result about the skin feature; and
update the database to include the skin feature and the clinical result.

8. The system of claim 1, wherein the results include an image of a skin feature and the memory further encodes computer executable instructions that, when executed by the at least one processor, cause the at least one processor to:
receive an annotation for the image of the skin feature, the annotation being at least one of: a diagnosis, a biopsy result, and a recommended review interval; and
add the annotation to the metadata of the image of the skin feature in the database.

9. A system for analyzing images of skin features, comprising:
at least one processor;
a database; and
memory comprising computer-executable instructions that, when executed by the at least one processor, cause the at least one processor to:
receive an image of a skin feature;
analyze the skin feature for at least one aspect of a plurality of aspects including: symmetry, border, color, diameter, evolution, and height;
identify a reference skin feature in the database, wherein the at least one aspect of the reference skin feature was previously analyzed;
compare the at least one aspect of the skin feature to the at least one aspect of the reference skin feature;
determine a risk ranking of the skin feature based on the comparison;
use the risk ranking to determine a highest-risk skin feature; and
generate guidance to a clinician based on the risk ranking, wherein the guidance includes a listing of skin features in order of the highest-risk skin feature to lowest risk.

10. The system of claim 9, wherein the guidance includes instructions to monitor the skin feature over time.

11. The system of claim 9, wherein the image of the skin feature is a composite image generated by combining multiple adjacent images into a larger image.

12. The system of claim 9, wherein the database includes a time-series of differential images of the reference skin feature.

* * * * *